(12) United States Patent
Geiger et al.

(10) Patent No.: US 9,109,186 B2
(45) Date of Patent: Aug. 18, 2015

(54) FRAGRANCE COMPOUNDS AND COMPOSITIONS

(75) Inventors: Marius Geiger, Winterthur (CH); Martin Lovchik, Dübendorf (CH)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 14/240,141

(22) PCT Filed: Sep. 6, 2012

(86) PCT No.: PCT/EP2012/067449
§ 371 (c)(1),
(2), (4) Date: Feb. 21, 2014

(87) PCT Pub. No.: WO2013/034657
PCT Pub. Date: Mar. 14, 2013

(65) Prior Publication Data
US 2014/0221263 A1   Aug. 7, 2014

(30) Foreign Application Priority Data

Sep. 7, 2011   (GB) .................................. 1115409.3

(51) Int. Cl.
*C07C 47/11* (2006.01)
*C11B 9/00* (2006.01)
*C07C 47/225* (2006.01)

(52) U.S. Cl.
CPC ............... *C11B 9/003* (2013.01); *C07C 47/225* (2013.01); *C07C 2101/08* (2013.01)

(58) Field of Classification Search
CPC .............................. C07C 47/225; C11B 9/003
USPC ............................................. 568/420; 512/8
See application file for complete search history.

(56) References Cited

U.S. PATENT DOCUMENTS 5,073,538 A   12/1991   Heullmann et al.
6,441,052 B1   8/2002   Bajgrowicz et al.

FOREIGN PATENT DOCUMENTS

EP           0 093 425 A1    11/1983
WO    WO 2008/068310 A1    6/2008

OTHER PUBLICATIONS

PCT/EP2012/067449—International Search Report, mailed Nov. 23, 2012.
PCT/EP2012/067449—International Written Opinion, mailed Nov. 23, 2012.
PCT/EP2012/067449—International Preliminary Report on Patentability, issued Mar. 12, 2014.
GB 1115409.3—Great Britain Search Report, mailed Dec. 22, 2011.

*Primary Examiner* — John Hardee
(74) *Attorney, Agent, or Firm* — Curatolo Sidoti Co., LPA; Joseph G. Curatolo; Salvatore A. Sidoti

(57) ABSTRACT

Compounds of formula (I)

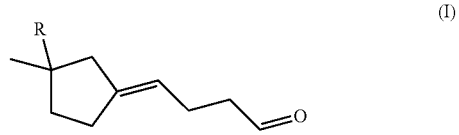

wherein R is methyl or ethyl, having floral, green odor notes, their use as fragrance and perfumed products comprising them.

6 Claims, No Drawings

FRAGRANCE COMPOUNDS AND COMPOSITIONS

CROSS REFERENCE TO RELATED APPLICATIONS

This application is a national stage application of International Application No. PCT/EP2012/067449, filed 6 Sep. 2012, which claims priority from Great Britain Patent Application No. 1115409.3, filed 7 Sep. 2011, from which applications priority is claimed, and which are incorporated herein by reference.

The present invention relates to substituted 4-cyclopentylidenebutanals having floral, green odor notes, and to their use as flavor and fragrance ingredient and to compositions and products comprising them. It furthermore relates to a method of their production.

Floral, green odor characteristics are important scents in perfumery. Albeit a wide range of compounds possessing floral, green odor notes are known, there is a constant demand for new compounds that enhance, modify or improve on odor notes.

It has now been found that certain substituted 4-cyclopentylidenebutanals have much sought-after floral, muguet and green odour notes.

Accordingly, in a first aspect there is provided the use as flavour or fragrance of a compound of formula (I)

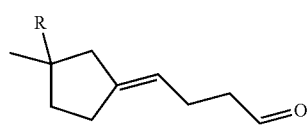

(I)

wherein R is methyl or ethyl.

The compounds of formula (I) may be used alone, as mixtures thereof, or in combination with a base material. As used herein, the "base material" includes all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, "fragrance composition" means any composition comprising at least one compound of formula (I) and a base material, e.g. a diluent conventionally used in conjunction with odorants, such as dipropylene glycol (DPG), isopropyl myristate (IPM), triethyl citrate (TEC) and alcohol (e.g. ethanol), and known odorants.

The following list comprises examples of known odorant molecules, which may be combined with the compounds of the present invention:

essential oils and extracts, e.g. castoreum, costus root oil, oak moss absolute, geranium oil, tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol™, eugenol, farnesol, geraniol, Javanol™, linalool, menthol, nerol, phenylethyl alcohol, rhodinol, Sandalore™, Super Muguet™, terpineol or Timberol™;

aldehydes and ketones, e.g. Azurone® (7-(3-methylbutyl)-1,5-benzodioxepin-3-one), anisaldehyde, α-amylcinnamaldehyde, Georgywood™, hydroxycitronellal, Iso E® Super, Isoraldeine®, Hedione®, Lilial®, maltol, methyl cedryl ketone, methylionone, verbenone or vanillin;

ethers and acetals, e.g. Ambrox™, geranyl methyl ether, rose oxide or Spirambrene™;

esters and lactones, e.g. benzyl acetate, cedryl acetate, γ-decalactone, Helvetolide®, γ-undecalactone or vetivenyl acetate;

macrocycles, e.g. Ambrettolide®, ethylene brassylate or Exaltolide®;

heterocycles, e.g. isobutylquinoline.

The compounds according to formula (I) may be used in a broad range of perfumed products, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients. The proportion is typically from 0.0001 to 5 weight percent of the application. In one embodiment, compounds of the present invention may be employed in a fabric softener in an amount of from 0.0001 to 0.05 weight percent. In another embodiment, compounds of the present invention may be used in fine perfumery in amounts from 0.01 to 3 weight percent, more preferably between 0.5 and 2 weight percent. However, these values are given only by way of example, since the experienced perfumer may also achieve effects or may create novel accords with lower or higher concentrations, e.g. up to about 10 weight percent based on the perfumed product.

The compounds as described hereinabove may be employed in a consumer product base simply by directly mixing at least one compound of formula (I), or a fragrance composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base.

Thus, the invention additionally provides a method of manufacturing a perfumed product, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactorily acceptable amount of at least one compound of the present invention as hereinabove described the odor notes of a consumer product base will be improved, enhanced, or modified.

Thus, the invention furthermore provides a method for improving, enhancing or modifying a consumer product base by means of the addition thereto of an olfactorily acceptable amount of at least one compound of formula (I).

The invention also provides a perfumed product comprising:
a) as odorant at least one compound of formula (I); and
b) a consumer product base.

As used herein, "consumer product base" means a composition for use as a consumer product to fulfill specific actions, such as cleaning, softening, caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body-care products, e.g. shampoo, shower gel; air care products and cosmetics, e.g. deodorant, vanishing creme. This list of products is given by way of illustration and is not to be regarded as being in any way limiting.

To the best of our knowledge none of the compounds falling within the definition of formula (I) are described in the literature and are thus novel in their own right.

Accordingly, the present invention refers in a further aspect to compounds of formula (I)

wherein R is methyl or ethyl.

The compounds of formula (I) may comprise a chiral center and as such may exist as a mixture of stereoisomers, or may be resolved in isomerically pure forms. Resolving stereoisomers adds to the complexity of manufacture and purification of these compounds and so it is preferred to use the compound as mixture of their stereoisomers simply for economic reasons. However, if it is desired to prepare individual stereoisomers, this may be achieved according to methods known in the art, e.g. preparative HPLC and GC, crystallization or stereoselective synthesis In particular embodiments compounds of formula (I) are selected from the group consisting of 4-(3,3-dimethylcyclopentylidene)butanal [(Z)-4-(3,3-dimethylcyclopentylidene) butanal and (E)-4-(3,3-dimethylcyclopentylidene)butanal) or mixtures thereof] and 4-(3-ethyl-3-methylcyclopentylidene) butanal [(Z)-4-(3-ethyl-3-methylcyclopentylidene)butanal and (E)-4-(3-ethyl-3-methylcyclopentylidene)butanal or mixtures thereof].

The compounds of formula (I) may be prepared starting from 3-methylcyclopent-2-enone (1). Conjugate addition of the respective alkyl group by standard synthetic procedures affords 2. The allylic alcohols 3 are formed by reaction of the ketone carbonyl (2) with vinyl organometallic reagent e.g. Grignard reagent and then transformed into vinyl ethers, which rearrange to compounds of formula (I) as depicted in Scheme 1. Further particulars as to reaction conditions are provided in the examples.

Scheme 1:

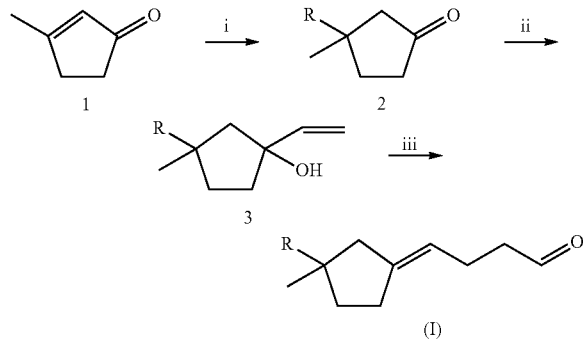

i) Cu(II), RMgCl; ii) CH$_2$CHMgBr; iii) CH$_2$CHOEt, H$^+$.

Pure or enriched E- or Z-isomers can be obtained via appropriate synthetic procedures or physical separation of the mixture. Optically pure or enriched stereoisomers (enantiomers) may be obtained by resolution of racemates or by asymmetric synthesis methodologies known to one skilled in the art.

The invention is now further described with reference to the following non-limiting examples. These examples are for the purpose of illustration only and it is understood that variations and modifications can be made by one skilled in the art.

All products described in the examples were obtained starting from 3-methylcyclopent-2-enone (1) and are racemic mixtures of diastereomers or E/Z isomers.

The reported NMR spectra were measured in CDCl$_3$ at 400 MHz if not otherwise stated; chemical shifts (δ) are reported in ppm downfield from TMS; coupling constants J in Hz. The GC/MS analyses were run using a ZB-5 column, if not stated otherwise. Flash chromatography: Merck silica gel 60 (230-400 mesh). Samples for olfactory evaluation were purified by bulb-to-bulb distillation. All purified products were isolated as colorless oils, the purity of which was confirmed by GC/MS.

EXAMPLE 1

(E/Z)-4-(3,3-Dimethylcyclopentylidene)butanal (Ia)

a) 3,3-Dimethylcyclopentanone (2a)

The reactor was charged with 3-methylcyclopent-2-enone (1, 150 g, 1.56 mol) and THF (1.6 l) and CuCl$_2$ (2 g, 0.02 mol) was added. The solution was cooled to 10° C. and MeMgCl 3M in THF (520 ml, 1.56 mol) was added dropwise over 1 hour. The mixture was warmed to room temperature and stirred for 30 minutes. The reaction mixture was poured onto aqueous NH$_4$Cl (25%, 300 g) and the mixture was stirred vigorously. Aqueous NH$_3$ (25%, 50 ml) was added and stirring was continued for 30 minutes. The deep blue mixture was placed in a separating funnel and the organic layer was removed. The aqueous layer was extracted with tert.-butyl methyl ether (2×100 ml).

The combined organic layers were washed with brine (200 ml) and concentrated in vacuo. The residue was purified by distillation over a 20 cm Vigreux column (b.p. 80° C. at 12 Torr) to afford 2a (78 g, 45% yield) as a colorless liquid.

$^1$H NMR: δ 2.31 (t, J=7.8, 2H); 2.05 (s, 1H); 1.79 (t, J=7.8, 2H); 1.12 (s, 6H). $^{13}$C NMR; δ 219.9 (s), 53.3 (t), 37.2 (t), 36.8 (t), 36.3 (s), 28.1 (2q).

MS: 112 (32, M$^+$), 97 (15), 83 (37), 69 (22), 57 (24), 56 (100), 55 (49), 42 (11), 41 (38), 39 (19).

b) 3,3-Dimethyl-1-vinylcyclopentanol (3a)

The reactor was charged with vinylmagnesium bromide (0.6M in THF, 245 ml, 147 mmol) and the solution was cooled to 5-10° C. 3,3-Dimethylcyclopentanone (2a, 15.0 g, 134 mmol) in THF (50 ml) was added over 10 minutes while keeping the temperature of the reaction mixture between 5-10° C. by means of an ice bath. The mixture was stirred for 30 minutes, then quenched with 10% AcOH (150 ml) and extracted with hexane (2×100 ml). The combined organic phases were washed with water, dried (MgSO$_4$), concentrated and distilled bulb-to-bulb to afford 3a (14.3 g, 76% yield) as a colorless liquid.

$^1$H NMR: δ 6 (dd, J=17.2, 10.6, 1H); 5.23 (dd, J=17.2, 1.3, 1H); 4.99 (dd, J=10.6, 1.3, 1H); 1.93-1.45 (m, 6H); 1.17 (s, 3H); 1.02 (s, 3H). $^{13}$C NMR: δ 145.3 (d), 110.5 (t), 83.1 (s), 55.0 (t), 40.4 (t), 40.0 (t), 38.6 (s), 31.1 (q), 30.7 (q).

MS: 140 (3, M$^+$), 97 (21), 84 (89), 83 (54), 70 (30), 69 (28), 57 (31), 56 (22), 55 (100), 43 (30), 41 (34).

c) (E/Z)-4-(3,3-Dimethylcyclopentylidene)butanal (Ia)

In a pressure vessel with stirrer (PARR 4842, 25 ml) a mixture of 3,3-dimethyl-1-vinylcyclopentanol (3a, 2 g, 14 mmol), ethyl vinyl ether (3.1 g, 43 mmol) and $H_3PO_4$ (0.01 g) were heated to 100° C. (pressure 2.5-2.7 bar) for 30 minutes. The temperature was then raised to 180° C. (pressure 5 bar) and maintained for 50 minutes. The reaction mixture was concentrated in vacuo and purified by flash chromatography (ethyl acetate/hexane 1:9) to afford Ia (1.5 g, 1:1 mixture of E/Z isomers, 63% yield) as a colorless liquid.

$^1$H NMR; mixture of E/Z isomers: δ 9.76 (m, 2H); 5.19 (m, 2H); 2.46 (m, 4H); 2.30 (m, 8H); 2.02 (s, 4H); 1.45 (m, 4H); 1.0 (s, 6H); 0.96 (s, 6H). $^{13}$C NMR; mixture of E/Z isomers: δ 202.6 (2d), 144.8 (s), 144.7 (s), 118.6 (d), 118.5 (d), 48.5 (t), 44.1 (t), 43.8 (t), 43.7 (t), 39.9 (t), 39.8 (t), 38.6 (s), 38.3 (s), 31.5 (2t), 28.1 (2q), 27.4 (2q), 22.5 (t), 22.1 (t).

MS: sum of E/Z isomers: 166 (1, M$^+$), 151 (43), 133 (46), 107 (100), 95 (70), 91 (29), 81 (51), 79 (49), 67 (46), 55 (55), 41 (55).

Odour description (mixture of E/Z isomers): floral, aldehydic, green, fatty, muguet.

Odour description (E isomer): floral, aldehydic, watery, fruity.

Odour description (Z isomer): floral, aldehydic, fresh, green, fatty, waxy.

EXAMPLE 2

(E/Z)-4-(3-Ethyl-3-methylcyclopentylidene)butanal (Ib)

a) 3-Ethyl-3-methylcyclopentanone (2b)

3-Methylcyclopent-2-enone (1, 35.0 g, 0.36 mol) was reacted with ethylmagnesium chloride (2M in THF, 218 ml, 0.44 mol) in the presence of 1 mol % $CuCl_2$ in THF (200 ml) as described in Example 1a. The crude product was distilled over a 15 cm Vigreux column (B.p. 50° C. at 5 Torr) to give 2b (32.0 g, 69% yield) as a colorless liquid.

$^1$H NMR: δ 2.28 (m, 2H); 2.14-1.93 (m, 2H); 1.87-1.70 (m, 2H); 1.45 (dd, J=14.9, 7.3, 2H); 1.04 (s, 3H); 0.90 (t, J=7.58, 3H). $^{13}$C NMR: δ 220.0 (s), 51.8 (t), 39.7 (s), 36.7 (t), 34.6 (t), 33.9 (t), 24.4 (q), 8.9 (2q).

MS: 126 (41, M$^+$), 97 (68), 70 (47), 69 (71), 56 (55), 55 (100), 42 (20), 41 (63), 39 (30), 27 (18).

b) 3-Ethyl-3-methyl-1-vinylcyclopentanol (3b)

3-Ethyl-3-methylcyclopentanone (2b, 30.0 g, 0.24 mol) was reacted with vinylmagnesium bromide (0.6M in THF, 285 ml, 0.29 mol), as described in Example 1b, to afford 3b (22.0 g, 2:1 mixture of diastereomers, 60% yield) as a colorless liquid.

$^1$H NMR, mixture of diastereomers: δ 5.99 (m, 2H); 5.25 (m, 1H); 5.21 (m, 1H); 5.00 (m, 1H); 4.98 (m, 1H); 1.90-1.28 (m, 18H); 1.13 (s, 3H); 0.96 (s, 3H); 0.90-0.82 (m, 6H). $^{13}$C NMR, mixture of diastereomers: δ 145.3 (d), 145.2 (d), 110.5 (2t), 82.7 (s), 82.6 (s), 53.2 (t), 53.0 (t), 42.1 (s), 41.9 (s), 40.2 (t), 39.8 (t), 38.1 (t), 37.8 (t), 36.1 (t), 35.7 (t), 27.8 (q), 26.9 (q), 9.5 (q), 9.3 (q).

MS, sum of diastereomers: 154 (1, M$^+$), 125 (30), 107 (34), 84 (91), 83 (45), 71 (26), 70 (31), 69 (40), 55 (100), 43 (37), 41 (30).

c) (E/Z)-4-(3-Ethyl-3-methylcyclopentylidene)butanal (Ib)

3-Ethyl-3-methyl-1-vinylcyclopentanol 3b (8.0 g, 52 mmol) was reacted with ethyl vinyl ether in a pressure reactor in the presence of $H_3PO_4$ (0.03 g), as described in Example 1c. Purification of the crude product by flash chromatography (ethyl acetate/hexane 1:9) afforded Ib (6.0 g, 1:1 mixture of E/Z isomers, 64% yield) as a colorless liquid.

$^1$H NMR; mixture of E/Z isomers: δ 9.76 (m, 2H); 5.18 (m, 2H); 2.46 (m, 4H); 2.28 (m, 8H); 2.11-1.93 (m, 4H); 1.55-1.23 (m, 8H); 0.91 (s, 3H); 0.87 (s, 3H); 0.86 (t, J=7.58, 3H); 0.84 (t, J=7.58, 3H). $^{13}$C NMR; mixture of E/Z isomers: δ 202.5 (2d), 144.6 (s), 144.5 (s), 118.5 (d), 118.4 (d), 46.8 (t), 43.8 (t), 43.7 (t), 42.3 (t), 42.1 (t), 41.6 (t), 37.8 (t), 37.6 (t), 33.9 (t), 33.3 (t), 31.1 (t), 27.0 (t), 24.3 (q), 23.6 (q), 22.5 (t), 22.2 (t), 9.3 (2q).

MS; sum of E/Z isomers: 180 (1, M$^+$), 151 (80), 133 (58), 107 (100), 95 (38), 91 (38), 81 (50), 79 (52), 67 (42), 55 (55), 41 (51).

Odour description (mixture of E/Z isomers): floral, aldehydic, slightly green, piney.

Odour description (E isomer): floral, green, transparent, freesia, aldehydic, sappy.

Odour description (Z isomer): floral, warm, fruity, peachy, leafy, violet.

EXAMPLE 3

Floral Perfuming Composition (Unisex)

| Ingredient | parts per weight |
|---|---|
| Phenyl Ethyl Alcohol (2-phenylethanol) | 12 |
| Cosmone (3-methyl-cyclotetradec-58-en-1-one) | 10 |
| Cyclohexal | 20 |
| Ethyl Linalool | 45 |
| Florosa (tetrahydro-2-isobutyl-4-methylpyran-4-ol) | 55 |
| Hedione (methyl 2-(2-butyl-3-oxocyclopentyl)acetate) | 450 |
| Hydroxy Citronellal | 25 |
| Cis Jasmone | 5 |
| Ethyl 2-Methylbutanoate @ 10% in DPG | 3 |
| Orange Essence | 25 |
| Raspberry Ketone (4-(4-hydroxyphenyl)butan-2-one) @ 10% in DPG | 15 |
| Cis-3-Hexenyl Salicylate | 55 |
| Serenolide (2-[1-(3,3-dimethylcyclohexyl)ethoxy]-2-methylpropyl cyclopropanecarboxylate) | 80 |
| (E/Z)-4-(3,3-Dimethylcyclopentylidene)butanal (Ia) | 25 |
| Dipropylene Glycol (DPG) | 175 |
| TOTAL | 1000 |

Addition of 25 parts per weight of compound Ia to the above composition results in a vibrant opening and enhancement of the exuberant orange, increasing the exotic florality and giving the composition a touch of sophistication.

The invention claimed is:
1. A compound of formula (I)

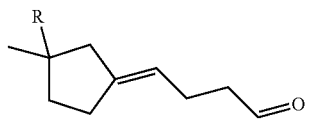

(I)

wherein R is methyl or ethyl.

2. The compound according to claim 1 selected from 4-(3,3-dimethyl cyclopentylidene)butanal and 4-(3-ethyl-3-methylcyclopentylidene)butanal.

3. A method of utilizing as flavour or fragrance ingredient a compound of formula (I)

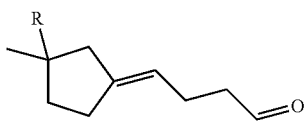

wherein R is methyl or ethyl, comprising adding the compound of formula (I) to a consumer product base.

4. A fragrance composition or a perfumed product comprising a compound of formula (I)

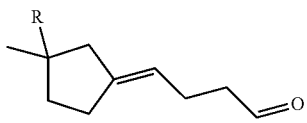

wherein R is methyl or ethyl.

5. The perfumed product according to claim 4 wherein the perfumed product is selected from fine perfumery, fabric care, household products, beauty and personal care products and air care products.

6. A method of improving, enhancing, or modifying a consumer product base comprising the step of adding thereto an olfactorily acceptable amount of at least one compound of formula (I)

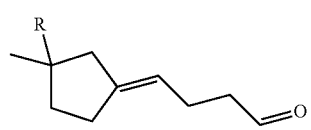

wherein R is methyl or ethyl.

* * * * *